(12) United States Patent
Sobolov-Jaynes et al.

(10) Patent No.: US 6,225,318 B1
(45) Date of Patent: May 1, 2001

(54) 4-AMINOQUINAZOLONE DERIVATIVES

(75) Inventors: Susan B. Sobolov-Jaynes, Ivoryton, CT (US); Lee D. Arnold, Westborough, MA (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/449,855

(22) Filed: Nov. 26, 1999

Related U.S. Application Data

(63) Continuation-in-part of application No. 08/953,078, filed on Oct. 17, 1997, now abandoned.
(60) Provisional application No. 60/028,881, filed on Oct. 17, 1996.

(51) Int. Cl.[7] .............. C07D 401/14; C07D 403/14; C07D 409/14; A61K 31/381; A61K 31/404
(52) U.S. Cl. ............................. 514/259; 544/284
(58) Field of Search .................... 544/283, 284, 544/293; 514/234.5, 259

(56) References Cited

U.S. PATENT DOCUMENTS

| | | | |
|---|---|---|---|
| 5,256,781 | 10/1993 | Primeau et al. | 544/293 |
| 5,457,405 | 10/1995 | Barker | 514/234.5 |
| 5,736,534 | * 4/1998 | Arnold | 514/63 |
| 5,747,498 | 5/1998 | Schnur et al. | 514/259 |
| 5,866,572 | 2/1999 | Barker et al. | 514/234.5 |

FOREIGN PATENT DOCUMENTS

| | | |
|---|---|---|
| 0414386 | 2/1991 | (EP) . |
| 0520722 | 12/1992 | (EP) . |
| 0566226 | 10/1993 | (EP) . |
| 0602851 | 6/1994 | (EP) . |
| 0635498 | 1/1995 | (EP) . |
| 0635507 | 1/1995 | (EP) . |
| 9220642 | 11/1992 | (WO) . |
| 9515758 | 6/1995 | (WO) . |
| 9519970 | 7/1995 | (WO) . |
| 9523141 | 8/1995 | (WO) . |
| 9609294 | 3/1996 | (WO) . |
| WO96/16960 | 6/1996 | (WO) . |
| WO96/30347 | 10/1996 | (WO) . |
| 9640142 | 12/1996 | (WO) . |
| WO97/22596 | 6/1997 | (WO) . |
| 9730044 | 8/1997 | (WO) . |
| WO97/30034 | 8/1997 | (WO) . |

OTHER PUBLICATIONS

Chem Abst: Myers et al., 1995: 780431.*
Chem Abst: Barker., 1995: 468620.*
Chem Abst; Barker., 1995: 446731.*

* cited by examiner

Primary Examiner—Mukund J. Shah
Assistant Examiner—Deepak R. Rao
(74) Attorney, Agent, or Firm—Peter C. Richardson; Paul H. Ginsburg; Jeffrey N. Myers

(57) ABSTRACT

This invention relates to certain 4-aminoquinazoline derivatives of the formula

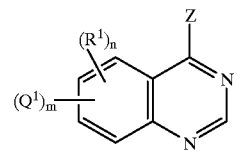

I and their pharmaceutically acceptable salts wherein $R^1$, $Q^1$, m, n, and Z are defined as in the specification. The compounds of formula I and pharmaceutically acceptable salts are useful for the treatment of hyperproliferative disorders and conditions in mammals.

6 Claims, No Drawings

4-AMINOQUINAZOLONE DERIVATIVES

The present application is a continuation-in-part of U.S. Ser. No. 08/953,078, filed Oct. 17, 1997, now abandoned, and claims priority under 35 USC 199(e) of U.S. Provisional Application 60/028,881 filed Oct. 17, 1996. The complete text and figures of all of the above applications are incorporated by reference herein, as if fully set forth.

BACKGROUND OF THE INVENTORS

This invention relates to 4-aminoquinoline derivatives that are useful in the treatment of hyperproliferative diseases such as cancers in mammals.

Many of the current treatment regimes for cancer utilize compounds which inhibit DNA synthesis. Such compounds are toxic to cells generally but their toxic effect on the rapidly dividing tumor cells can be beneficial. Alternative approaches to anti-cancer agents which act by mechanisms other than the inhibition of DNA synthesis have been explored in order to enhance the selectivity of action against cancer cells.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as a selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor.

Various other compounds, such as styrene derivatives, have also been shown to possess tyrosine kinase inhibitory properties. More recently, five European patent publications, namely EP 0 566 266 A1, published Oct. 20, 1993, EP 0 602 851 A1, published Jun. 22, 1994, EP 0 635 507 A1, published Jan. 25, 1995, EP 0 635 498 A1, published Jan. 25, 1995, and EP 0 520 722 A1, published Dec. 30, 1992, have referred to certain quinazoline derivatives as possessing anti-cancer properties that result from their tyrosine kinase inhibitory properties. Also, World Patent Application WO 92/20642, published Nov. 26, 1992, refers to certain bis-mono and bicyclic aryl and heteroaryl compounds as tyrosine kinase inhibitors that are useful in inhibiting abnormal cell proliferation. World Patent Application WO96/16960, published Jun. 6, 1996, and World Patent Application WO 95/23141, published Aug. 31, 1995, refer to certain phenylamino substituted quinazolines as tyrosine kinase inhibitors that are useful for the same purpose.

European patent publication EP 0 414 386 A1, published Feb. 27, 1991, refers to certain pyrido[2,3-d]pyrimidines as fungicides, insecticides and miticides.

Co-pending patent applications PCT/IB95/00436 and PCT/IB95/07881, which designate the United States and which were filed on Jun. 6, 1995 and Jun. 7, 1995, respectively, describe optionally substituted indolyl- and phenylamino-quinazolines, respectively, which are useful in the treatment of hyperproliferative diseases involving receptor tyrosine kinases.

Although the anti-cancer compounds described above make a significant contribution to the art there is a continuing search in this field of art for improved anti-cancer pharmaceuticals.

SUMMARY OF THE INVENTION

This invention relates to heterocyclic substituted aniline derivatives of the formula

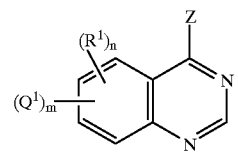

I wherein Z is $NR^3R^4$, wherein $R^3$ is hydrogen and $R^4$ is either $Q^2$ or phenyl substituted with $(R^5)_q$, or $NR^3R^4$ is a group of the formula

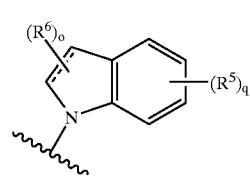

A wherein the dotted line represents an optional double bond;

each $R^5$ is independently selected from mono-, di- and tri-fluoromethyl, halo, nitro, hydroxy, amino, azido, isothiocyano, $(C_1-C_4)$alkyl, phenyl, thienyl, $(C_1-C_4)$alkoxy, benzyloxy, phenoxy, $(C_2-C_6)$alkenyl, $(C_2-C_6)$alkynyl, $(C_1-C_4)$alkylenedioxy, cyano, benzoylamino, trifluoromethylcarbonylamino, $(C_1-C_4)$alkanoylamino, $(C_1-C_4)$alkanoyl, N-mono- and N,N-di-$(C_1-C_4)$alkylamino, $(C_1-C_4)$alkylsulfonylamino, trifluoromethylsulfonylamino, $(C_1-C_4)$alkylthio, $(C_1-C_4)$alkylsulfinyl and $(C_1-C_4)$alkylsulfonyl, pyrrol-1-yl, piperidin-1-yl and pyrrolidin-1-yl, wherein said phenyl, benzyloxy, phenoxy and benzoylamino may optionally be mono-substituted with halo, nitro, trifluoromethyl, hydroxy or $(C_1-C_4)$alkyl, and wherein said $(C_1-C_4)$alkylenedioxy is linked at both ends to adjacent carbons on the benzene moiety;

or two $R^5$'s, together with the carbons atoms to which they are attached, form a group selected from imidazolyl, pyrrolo and pyrazolyl;

each $R^6$ is independently selected from hydroxy, amino, N-mono- and N,N-di-$(C_1-C_4)$alkylamino, sulfo and $(C_1-C_4)$alkoxy (provided that such groups are not attached to a ring carbon which is directly adjacent to the ring nitrogen), or each $R^6$ is independently selected from carboxy, hydroxy$(C_1-C_4)$alkyl, $(C_1-C_4)$alkoxy $(C_1-C_4)$alkyl, amino$(C_1-C_4)$alkyl, mono-N- and di-N, N-$(C_1-C_4)$alkylamino$(C_1-C_4)$alkyl, morpholino $(C_1-C_4)$alkyl, 4-$(C_1-C_4)$alkyl-piperazin-1-yl$(C_1-C_4)$alkyl, carboxy$(C_1-C_4)$alkyl, $(C_1-C_4)$alkoxycarbonyl, sulfo$(C_1-C_4)$alkyl, pyridyl$(C_1-C_4)$alkyl and $(C_1-C_4)$alkyl;

q is an integer from 0 to 3;

o is 0, 1 or 2;

$Q^2$ is a 9- or 10-membered bicyclic heteroaryl cyclic moiety, or a hydrogenated derivative thereof, containing one or two nitrogen heteroatoms and optionally containing a further heteroatom selected from nitrogen, oxygen and sulphur, and $Q^2$ may optionally bear one or two substituents independently selected from halogeno, hydroxy, oxo, amino, nitro, carbamoyl, $(C_1-C_4)$alkyl, $(C_1-C_4)$alkoxy, $(C_1-C_4)$alkylamino, di-$[(C_1-C_4)$alkyl]amino, $(C_2-C_4)$alkanoylamino, $(C_2-C_4)$alkenyl and $(C_2-C_4)$alkynyl;

$Q^1$ is Ar-Y—X;

each Ar is a monocyclic or bicyclic aryl or heteroaryl ring (e.g., phenyl, naphthyl, pyridyl, pyrimidyl, furanyl, thiophenyl, pyrrolyl, oxazolyl, thiazelyl, benzimidazolyl, benzoxazolyl, benzthiazolyl, pyranyl, pyrazinyl, thiazinyl, indolyl, isoindolyl, benzofuranyl, benzothienyl, quinazolinyl, pterinyl, quinolinyl or isoquinolinyl), and wherein each Ar group may optionally be substituted with from one to three substituents $R^2$;

each X is, independently, $C_2$ alkene (i.e., —C=C—), $C_2$ alkyne (i.e., —C≡C—) or absent;

m is one or two;

n is zero, one, two or three;

Y is $(CH_2)_p$ wherein p is 0–5 and wherein one or two of the $CH_2$ groups may optionally and independently be replaced by either oxygen, sulfur, $SO_2$, C=O, NH, or $NCH_3$;

each $R^1$ is selected, independently, from:
(a) trifluoromethyl, halo, nitro, hydroxy, amino, cyano, $(C_1-C_4)$alkyl, $(C_1-C_4)$alkoxy, $(C_1-C_4)$alkoxycarbonyl, thio, $(C_1-C_4)$alkanoyloxy, $(C_1-C_4)$alkanoylamino, carboxy, phenoxy, benzoyloxy, carbamoyl, mono-N- and di-N-N-di-$(C_1-C_4)$alkylcarbamoyl, mono-N- and di-N,N-$(C_1-C_4)$alkylamino, mono-N and di-N,N-(hydroxy$(C_2-C_4)$alkyl)amino, mono-N and di-N,N-(($C_1-C_4$)alkoxy$(C_2-C_4)$alkyl)amino, anilino, pyrrolidin-1-yl, piperidin-1-yl, morpholino, piperazin-1-yl, 4-$(C_1-C_4)$alkylpiperazin-1-yl, $(C_1-C_4)$alkylthio and phenylthio, and any of the foregoing $R^1$ groups substituted on $(C_1-C_4)$alkyl; and
(b) hydroxy$(C_2-C_4)$alkoxy$(C_1-C_4)$alkyl, $(C_1-C_4)$alkoxy-$(C_2-C_4)$alkoxy-$(C_1-C_4)$alkyl, hydroxy $(C_2-C_4)$alkylthio$(C_1-C_4)$alkyl, $(C_1-C_4)$alkoxy $(C_2-C_4)$alkylthio$(C_1-C_4)$alkyl, hydroxyamino, benzoylamino, mono-N and di-N,N-$(C_1-C_4)$alkylcarbamoylmethylamino, carbamoylmethylamino, $(C_1-C_4)$alkoxycarbonylamino, $(C_1-C_4)$alkanoylamino, carboxymethylamino, $(C_1-C_4)$alkoxycarbonylmethylamino, $(C_1-C_4)$alkoxyamino, $(C_2-C_4)$alkanoyloxyamino, phenyl$(C_1-C_4)$alkylamino, $(C_1-C_4)$alkylsulphonylamino, benzenesulphonamido, 3-phenylureido, 2-oxopyrrolidin-1-yl, 2,5-dioxopyrrolidin-1-yl, ureido, $(C_1-C_4)$alkoxy$(C_1-C_4)$alkylcarbonylamino, $(C_1-C_4)$alkylsulfinyl, $(C_1-C_4)$alkylsulfonyl, $(C_1-C_4)$alkoxy$(C_2-C_4)$alkylthio, mono-, di- and trifluoromethyloxy, $(C_1-C_4)$alkylenedioxy, benzyloxy, azido, guanidino, aminocarbonyl, mono-N- and di-N,N-$(C_1-C_4)$alkylaminocarbonyl, phenyl $(C_1-C_4)$alkoxy, carboxymethoxy, $(C_1-C_4)$alkoxycarbonylmethoxy, carbamoylmethoxy, mono-N and di-N,N-$(C_1-C_4)$alkyl-carbamoylmethoxy, mono-N- and di-N,N-(hydroxy $(C_2-C_4)$alkyl)carboxamido, mono-N- and di-N,N-(($C_1-C_4$)alkoxy$(C_2-C_4)$alkyl)carboxamido and bis (($C_1-C_4$)alkanesulfonyl)amido; and
(c) $(C_2-C_4)$alkoxy, $(C_2-C_4)$alkylthio, $(C_2-C_4)$alkanoyloxy, $(C_2-C_4)$alkylamino, $(C_1-C_4)$alkyl $(C_1-C_4)$alkylenedioxy and $(C_2-C_4)$alkanoylamino; wherein each of the foregoing $R^1$ groups in "c" may optionally be substituted with one or two substituents independently selected from amino, halo, hydroxy, $(C_2-C_4)$alkanoyloxy, $(C_1-C_4)$alkoxy, mono-N- and di-N,N-$(C_1-C_4)$alkylamino, mono-N and di-N,N-(hydroxy$(C_2-C_4)$alkyl)amino, mono-N and di-N,N-(($C_1-C_4$)alkoxy$(C_2-C_4)$alkyl)amino, $(C_1-C_4)$alkanoylamino, phenoxy, anilino, imidazol-1-yl, phenylthio, piperidino, morpholino, piperazin-1-yl, 4-$(C_1-C_4)$alkylpiperazin-1-yl, carboxy, $(C_1-C_4)$alkoxycarbonyl, carbamoyl, mono-N- and di-N,N-$(C_1-C_4)$alkylcarbamoyl, carboxamido, mono-N- and di-N,N-$(C_1-C_4)$alkylcarboxamido and mono-N- and di-N,N-(hydroxy$(C_2-C_4)$alkyl) carboxamido;

wherein any phenyl moiety in an $R^1$ substituent may optionally be substituted with one or two substituents independently selected from halo, nitro, trifluoromethyl, hydroxy, $(C_1-C_4)$alkoxy and $(C_1-C_4)$alkyl, and wherein said $(C_1-C_4)$alkylenedioxy is linked at both ends to the quinazoline ring; and each $R^2$ is independently selected from the substituents listed above in paragraphs "(a)" and "(b)" of the definition of $R^1$;

with the proviso that: (a) $Q^1$ must be at position "6" or "7" of the quinazoline ring or at both of these positions; (b) Ar can not be unsubstitued phenyl; and (c) the sum of m+n can not be greater than four; (d) when $R^4$ is 1H-indol-5-yl and n is zero and m is one and $Q^1$ is a 2-(substituted-phenyl)-ethen-1-yl group that is attached to position "7" of the quinazoline ring, then (i) Ar can not be 1,1-dimethyl-4,4-dimethyl-1,2,3,4-tetrahydro-naphth-1-yl, and (ii) the phenyl moiety of $Q^1$ can not have any of the following 13 substitution patterns, each of which fully and independently defines the substitution on the phenyl moiety: 3-nitro, 4-methoxy, 4-bromo, 3,4-dimethoxy, 3-bromo, 4-hydroxymethyl, 2,3,4,5,6-pentafluoro, 3,5-methoxy, 1-aminoethyl, 3-oxo-4-methyl, 2-methoxy, 3-nitro-4-methylcarbonylamino or 3-methoxy-4-benzyloxy; and (e) when $R^4$ is 1H-indol-5-yl and n is one and m is one and $R^1$ is 6-methoxy and $Q^1$ is a 2-(substituted phenyl)-ethen-1-yl that is attached to position "7" of quinazoline ring, then (i) Ar can not be 1,1-dimethyl-4,4-dimethyl-1,2,3,4-tetrahydro-naphth-1-yl, and (ii) the phenyl moiety of $Q^1$ can not have any of the following 4 substitution patterns, each which fully and independently defines the substitution on the phenyl moiety; 3-nitro, 3-bromo, 4-bromo, or 2,3,4,5,6-pentafluoro; and the pharmaceutically acceptable salts of such compounds.

Preferred compounds of the formula I include the following:

(3-Ethynyl-phenyl)-(6-pyridin-2-yl-quinazolin-4-yl)-amine;
(3-Ethynyl-phenyl)-(6-pyridin-3-yl-quinazolin-4-yl)-amine;
(1H-Indol-5-yl)-(6-pyridin-3-yl-quinazolin-4-yl)-amine;
(3-Ethynyl-phenyl)-[6-(2-pyridin-4-yl-vinyl)-quinazolin-4-yl]-amine;
(1H-Indol-5-yl)-[6-(2-pyridin-4-yl-vinyl)-quinazolin-4-yl]-amine;
(1H-Indol-5-yl)-[7-methoxy-6-(2-pyridin-4-yl-vinyl)-quinazolin-4-yl]-amine;
(3-Oxazol-5-yl-phenyl)-[6-(2-pyridin-4-yl-vinyl)-quinazolin-4-yl]-amine;
(1H-Indol-5-yl)-[6-(2-pyridin-2-yl-vinyl)-quinazolin-4-yl]-amine;
(1H-Indol-5-yl)-(7-methoxy-6-pyridin-3-yl-quinazolin-4-yl)-amine;
(3-Ethynyl-phenyl)-(7-methoxy-6-pyridin-2-yl-quinazolin-4-yl)-amine;
(1H-Indol-5-yl)-(7-methoxy-6-pyridin-2-yl-quinazolin-4-yl)-amine;
(3-Bromo-phenyl)-(7-methoxy-6-pyridin-2-yl-quinazolin-4-yl)-amine;
4-(1H-Indol-5-ylamino)-6-pyridin-3-yl-quinazolin-7-ol;
(1H-Indol-5-yl)-(7-methoxy-6-pyridin-2-ylethynyl-quinazolin-4-yl)-amine;
(1H-Indol-5-yl)-[7-(2-methoxy-ethoxy)-6-pyridin-3-yl-quinazolin-4-yl]-amine;
(1H-Indol-5-yl)-{7-methoxy-6-[2-(4-methoxy-phenyl)-vinyl]-quinazolin-4-yl}-amine;
{6-[2-(3,4-Dimethoxy-phenyl)-vinyl]-7-methoxy-quinazolin-4-yl}-(1H-indol-5-yl)-amine;
(4-{2-[4-(1H-Indol-5-ylamino)-7-methoxy-quinazolin-6-yl]-vinyl}-phenyl)-methanol;
{6-[2-(4-Amino-phenyl)-vinyl]-7-methoxy-quinazolin-4-yl}-(1H-indol-5-yl)-amine;
(1H-Indol-5-yl)-[7-methoxy-6-(2-pyrazin-2-yl-vinyl)-quinazolin-4-yl]-amine;
(1H-Indol-5-yl)-{7-methoxy-6-[2-(6-methyl-1-oxy-pyridin-3-yl)-vinyl]-quinazolin-4-yl}-amine;
(6-{2-[4-(1-Amino-ethyl)-phenyl]-vinyl}-7-methoxy-quinazolin-4-yl)-(1H-indol-5-yl)-amine;
(1H-Indol-5-yl)-[6-(2-pyridin-2-yl-vinyl)-quinazolin-4-yl]-amine;
(1H-Indol-5-yl)-[7-methoxy-6-(6-methoxy-pyridin-3-yl)-quinazolin-4-yl]-amine;
{6-[2-(4-Amino-phenyl)-vinyl]-7-methoxy-quinazolin-4-yl}-(1H-indol-5-yl)-amine;
(1H-Indol-5-yl)-[7-methoxy-6-(1-oxy-pyridin-3-yl)-quinazolin-4-yl]-amine; and
[6-(3-Amino-phenylethynyl)-7-methoxy-quinazolin-4-yl]-(1H-indol-5-yl)-amine.

Examples of other compounds of the formula I are the following:

{6-[3-(Benzyl-methyl-amino)-prop-1-ynyl]-quinazolin-4-yl}-(1H-indol-5-yl)-amine;
(3-Ethynyl-phenyl)-(6-pyridin-2-ylethynyl-quinazolin-4-yl)-amine;
(1H-Indol-5-yl)-(6-pyridin-2-ylethynyl-quinazolin-4-yl)-amine;
(1H-Indol-5-yl)-(7-methoxy-6-pyridin-2-ylethynyl-quinazolin-4-yl)-amine;
(3-Ethynyl-phenyl)-(6-pyridin-2-yl-quinazolin-4-yl)-amine;
(3-Ethynyl-phenyl)-[6-(4-methylsulfanyl-phenyl)-quinazolin-4-yl]-amine;
(3-Ethynyl-phenyl)-[6-(4-trifluoromethyl-phenyl)-quinazolin-4-yl]-amine;
(3-Ethynyl-phenyl)-(7-methoxy-6-phenyl-quinazolin-4-yl)-amine;
(3-Ethynyl-phenyl)-(7-methoxy-6-pyridin-3-yl-quinazolin-4-yl)-amine;
(3-Ethynyl-phenyl)-(7-methoxy-6-pyridin-2-yl-quinazolin-4-yl)-amine;
(3-Bromo-phenyl)-(6-pyridin-2-yl-quinazolin-4-yl)-amine;
2-[4-(1H-Indol-5-ylamino)-7-methoxy-quinazolin-6-yl]-benzoic acid ethyl ester;
2-[4-(3-Ethynyl-phenylamino)-7-methoxy-quinzaolin-6-yl]-benzoic acid ethyl ester;
4-[4-(1H-Indol-5-ylamino)-7-methoxy-quinazolin-6-yl]-benzoic acid ethyl ester;
4-(1H-Indol-5-ylamino)-6-pyridin-3-yl-quinazolin-7-yl)-amine;
(1H-Indol-5-yl)-[7-(2-methoxy-ethoxy)-6-pyridin-3-yl-quinazolin-4-yl]-amine;
(3-Ethynyl-phenyl)-(6-p-tolyl-quinazolin-4-yl)-amine;
(3-Ethynyl-phenyl)-(6-phenyl-quinazolin-4-yl)-amine;
(3-Ethynyl-phenyl)-[6-(4-methylsulfanyl-phenyl)-quinazolin-4-yl]-amine;
(3-Ethynyl-phenyl)-[6-(4-trifluoromethyl-phenyl)-quinazolin-4-yl]-amine;
[6-(4-Chloro-phenyl)-quinazolin-4-yl]-(3-ethynyl-phenyl)-amine;
4-(6-Chloro-2,3-dihydro-indol-1-yl)-6-phenyl-quinazoline;
(3-Ethynyl-phenyl)-(7-methoxy-6-phenyl-quinazolin-4-yl)-amine;
4-(6-Chloro-2,3-dihydro-indol-1-yl)-7-methoxy-6-phenyl-quinazoline;
(3-Oxazol-5-yl-phenyl)-(6-pyridin-3-yl-quinazolin-4-yl)-amine;
(1H-Indol-5-yl)-[6-(2-pyridin-4-yl-ethyl)-quinazolin-4-yl]-amine;
(1H-Indol-5-yl)-(6-phenylethynyl-quinazolin-4-yl)-amine;
(1H-Indol-5-yl)-(7-methoxy-6-pyridin-3-yl-quinazolin-4-yl)-amine
(3-Ethynyl-phenyl)-(7-methoxy-6-pyridin-3-yl-quinazolin-4-yl)-amine;
4-[4-(1H-indol-5-ylamino)-quinazolin-6-yl]-benzoic acid ethyl ester;
2-[4-(3-Ethylnyl-phenylamino)-quinazolin-6-yl]-benzoic acid ethyl ester;
2-[4-(1H-Indol-5-ylamino)-quinazolin-6-yl]-benzoic acid ethyl ester;
(3-Ethynyl-phenyl)-(6-pyridin-2-ylethynyl-quinozoline-4-yl)-amine;

(1H-Indol-5-yl)-(6-pyridin-2-yl-quinazolin-4-yl)-amine;

(3-Bromo-phenyl)-(6-pyridin-2-yl-quinazolin-4-yl)-amine;

(1H-Indol-5-yl)-(6-pyridin-2-ylethynyl-quinazolin-4-yl)-amine;

2-[4-(1H-Indol-5-ylamino)-7-methoxy-quinazolin-6-yl]-benzoic acid ethyl ester;

2-[4-(3-Ethynyl-phenylamino)-7-methoxy-quinazolin-6-yl]-benzoic acid ethyl ester;

4-[4-(1H-Indol-5-ylamino)-7-methoxy-quinazolin-6-yl]-benzoic acid ethyl ester;

(1H-Indol-5-yl)-(7-methoxy-6-styryl-quinazolin-4-yl)-amine;

(1H-Indol-5-yl)-{7-methoxy-6-[2-(3-nitro-phenyl)-vinyl]-quinazolin-4-yl}-amine;

{6-[2-(4-Benzyloxy-3-methoxy-phenyl)-vinyl]-7-methoxy-quinazoline-4-yl}-(1H-indol-5-yl)-amine;

(1H-Indol-5-yl)-[7-methoxy-6-(2-pyridin-2-yl-vinyl)-quinazolin-4-yl]-amine;

(1H-indol-5-yl)-{7-methoxy-6-[2-(5,5,8,8-tetramethyl-5,6,7,8-tetrahydro-naphthalen-2-yl)-vinyl]-quinazolin-4-yl}-amine;

N-(4-{2-[4-(1H-Indol-5-ylamino)-7-methoxy-quinazolin-6-yl]-vinyl}-2-nitro-phenyl)-acetamide;

{6-[2-(3,5-Dimethoxy-phenyl)-vinyl]-7-methoxy-quinazolin-4-yl}-(1H-indol-5-yl)-amine;

(4-{2-[4-(1H-Indol-5-ylamino)-quinazolin-6-yl]-vinyl}-phenyl)-amine;

(1H-Indol-5-yl)-[6-(2-pyrazin-2-yl-vinyl)-quinazolin-4-yl]-amine;

5-[4-(1H-Indol-5-ylamino)-quinazolin-6-yl]-1H-pyridin-2-one;

(1H-Indol-5-yl-5-yl)-[7-methoxy-6-(6-methyl-pyridin-3-yl)-quinazolin-4-yl]-amine;

5-[4-(1H-Indol-5-ylamino)-7-methoxy-quinazolin-6-yl]-nicotinamide;

5-[4-(1H-Indol-5-ylamino)-7-methoxy-quinazolin-6-yl]-nicotinonitrile;

5-[4-(1H-Indol-5-ylamino)-7-methoxy-quinazolin-6-yl] pyridin-3-yl-methanol;

5-[4-(1H-Indol-5-ylamino)-7-methoxy-quinazolin-6-yl]-nicotinic acid methyl ester;

(1H-Indol-5-yl)-(7-methoxy-6-quinolin-3-yl-quinazolin-4-yl)-amine;

[6-(6-Amino-pyridin-3-yl)-7-methoxy-quinazolin-4-yl]-(1H-indol-5-yl)-amine;

[6-(6-Dimethyl-pyridin-3-yl)-7-methoxy-quinazolin-4-yl]-(1H-indol-5-yl)-amine;

5-(6-Pyridin-3-yl-quinazolin-4-ylamino)-1,3-dihydro-indol-2-one;

(1H-Indol-5-yl)-(7-methoxy-6-pyrazin-2-yl-quinazolin-4-yl)-amine;

(1H-Indol-5-yl)-[7-methoxy-6-(6-methyl-pyrazin-2-yl)-quinazolin-4-yl]-amine;

[6-(6-Amino-pyrazin-2-yl)-7-methoxy-quinazolin-4-yl]-(1H-indol-5-yl)-amine; and (1H-Indol-5-yl)-[6-(2-pyrazin-2-yl-vinyl)-quinazolin-4-yl]-amine.

This invention also relates to a method of inhibiting abnormal cell growth in mammals, including humans, that is caused by the mutation or overexpression of a protein tyrosine kinase (e.g., epidermal growth factor receptor tyrosine kinase), which comprises administering to a mammal in need of such inhibition a protein tyrosine kinase inhibiting effective amount of a compound of the formula I, or a pharmaceutically acceptable salt thereof.

This invention also relates to a pharmaceutical composition for inhibiting abnormal cell growth in mammals, including humans, that is caused by the mutation or overexpression of a protein tyrosine kinase (e.g., epidermal growth factor receptor tyrosine kinase), comprising a protein tyrosine kinase inhibiting effective amount of a compound according to claim 1, or a pharmaceutically acceptable salt thereof, and a pharmaceutically acceptable carrier.

This invention also relates to a method of treating or preventing hyperproliferative disorders or conditions such as malignant or benign tumors, other hyperplastic conditions such as benign hyperplasia of the skin (e.g., psoriasis) and benign hyperplasia of the prostate (e.g., benign prostatic hypertrophy (BPH)), leukemias and lymphoid malignancies in a mammal, including a human, comprising administering to a mammal in need of such treatment or prevention an amount of a compound of the formula I, or a pharmaceutically acceptable salt thereof, that is effective in treating or preventing such disorder or condition.

This invention also relates to a pharmaceutical composition for preventing or treating hyperproliferative disorders or conditions, such as benign or malignant tumors, other hyperplastic conditions such as benign hyperplasia of the skin (e.g., psoriasis) and benign hyperplasia of the prostate (e.g., benign prostatic hypertrophy), leukemias and lymphoid malignancies in a mammal, including a human, comprising an amount of a compound of the formula I, or a pharmaceutically salt thereof, that is effective in preventing or treating such condition or disorder, and a pharmaceuticaly acceptable carrier.

This invention also relates to a method of treating or preventing hyperproliferative disorders or conditions such as malignant or benign tumors, other hyperplastic conditions such as benign hyperplasia of the skin (e.g., psoriasis) and benign hyperplasia of the prostate (e.g., benign prostatic hypertrophy), leukemias and lymphoid malignancies in a mammal, including a human, comprising administering to a mammal in need of such treatment or prevention a protein tyrosine kinese inhibiting effective amount of a compound of the formula I, or a pharmaceutically acceptable salt thereof.

This invention also relates to a pharmaceutical composition for preventing or treating hyperproliferative disorders or conditions, such as benign or malignant tumors, other hyperplastic conditions such as benign hyperplasia of the skin (e.g., psoriasis) and benign hyperplasia of the prostate (e.g., benign prostatic hypertrophy), leukemias and lymphoid malignancies in a mammal, including a human, comprising a protein tyrosine kinase inhibiting effective amount of a compound of the formula I, or a pharmaceutically salt thereof, and a pharmaceutically acceptable carrier.

Examples of such benign proliferative disorders that can be prevented or treated with compounds of the formula II and their pharmaceutically acceptable salts are psoriasis, benign prostatic hypertrophy and restinosis.

The term "alkyl", as used herein, unless otherwise indicated, includes saturated monovalent hydrocarbon radicals having straight, branched or cyclic moieties or combinations thereof.

The term "halo", as used herein, unless otherwise indicated, refers to chloro, fluoro, bromo or iodo.

The term "one or more substituents", as used herein, refers to from one to the maximum number of substituents possible based on the numbers of available bonding sites.

The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature, are capable of forming base salts with various pharmacologically acceptable cations. Examples of such salts include the alkali metal or alkaline earth metal salts and particularly, the sodium and potassium salts.

The compounds of formula I may contain chiral centers and therefore may exist in different enantiomeric forms. This invention relates to all optical isomers (e.g., enantiomers and diastereomers) and other stereoisomers of compounds of the formula I, as well as racemic and other mixtures thereof.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays.

Patients that can be treated with compounds of the formula I according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

Patients that can be treated with compounds of the formula I and their pharmaceutically acceptable salts according to the methods of this invention also include patients suffering from abnormal cell growth, as defined above.

This invention also relates to compounds of the formula

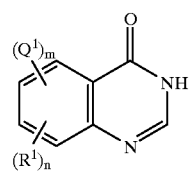

II wherein Ar, $Q^1$, m, $R^1$ and n are defined as above, except that the Ar group in $Q^1$ can not be phenyl. These compounds are useful as intermediates in the synthesis of compounds of the formula I.

DETAILED DESCRIPTION OF THE INVENTION

Compounds of the formula I may be prepared as described below. In the reaction schemes and discussion that follow, Z, A, $Q^1$, $Q^2$, Ar, X, Y, $R^1$ through $R^7$, m, n, o, p and q and formula I are defined as above.

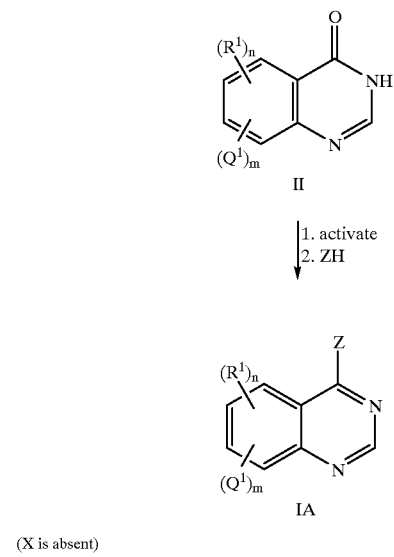

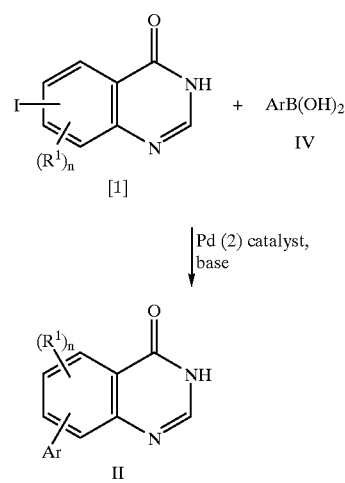

SCHEME 3
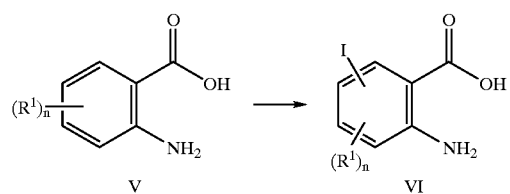
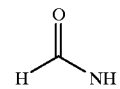
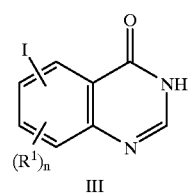
SCHEME 4
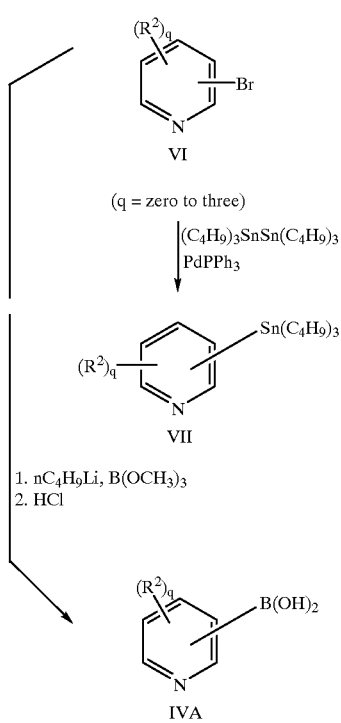
SCHEME 5
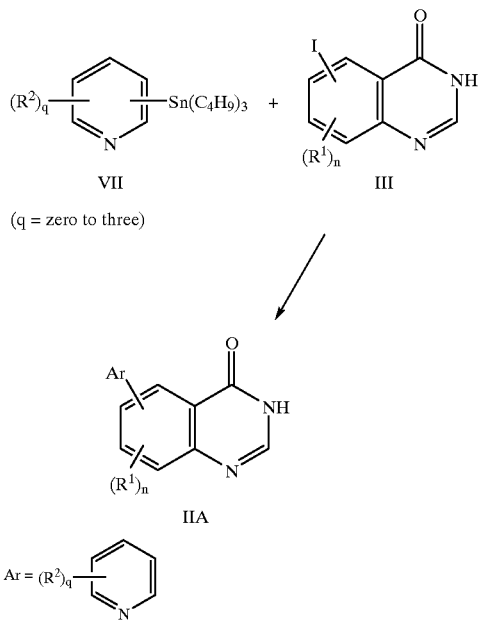
(q = zero to three)
SCHEME 6
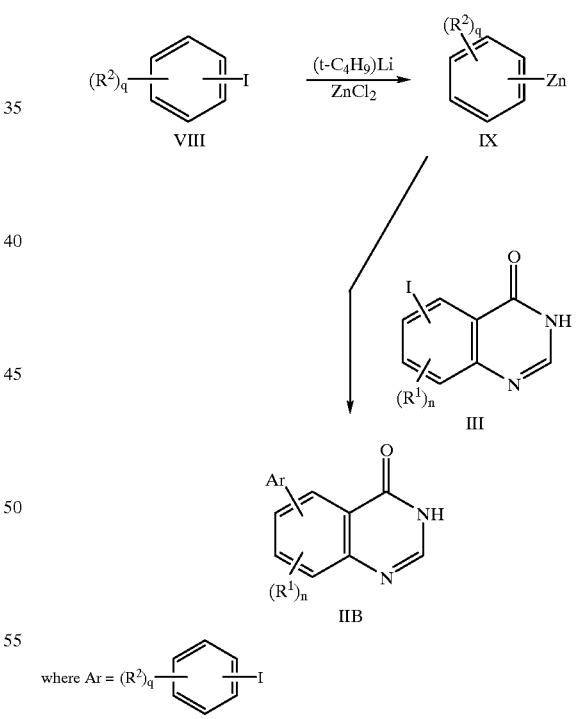

SCHEME 7

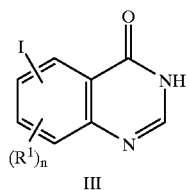
III 1. activate
2. ZH

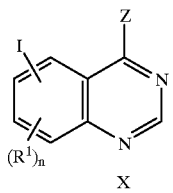
X

Ar—Y—XH

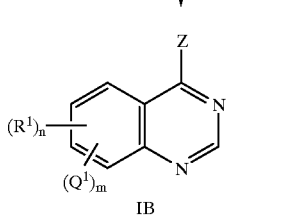
IB (X is C$_2$ alkene or C$_2$ alkyne)

SCHEME 8

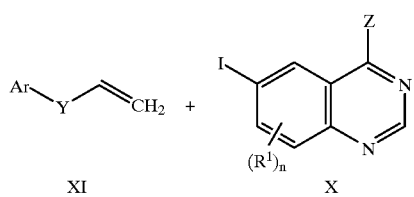

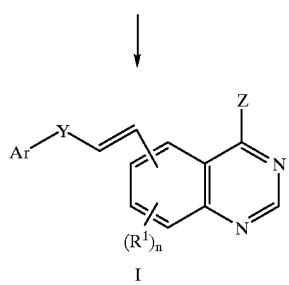
I

SCHEME 9

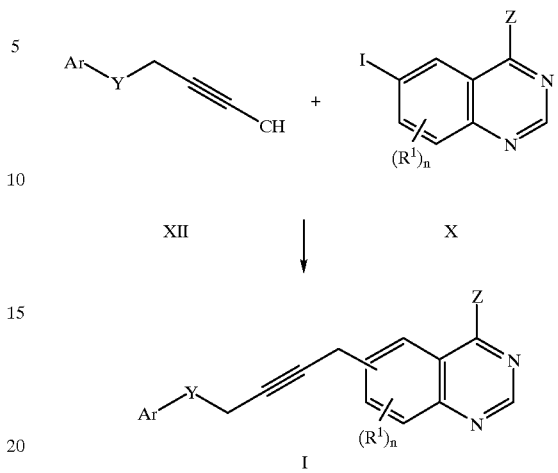

Scheme 1 illustrates the synthesis of compounds of the formula I wherein X is absent. These compounds are referred in Scheme 1 and throughout this specification as "compounds of the formula IA." As shown in Scheme 1, such compounds are prepared from the analogous compounds having an oxo group at position "4" of the quinazoline ring, the position to which Z is attached in the final product. Thus, compounds of the formula IA, all of which have the aryl or heteroaryl moieties of Q$^1$ attached directly to the quinazolinone ring, are formed by adding one or two Q$^1$ groups to the quizalinone nucleus prior to converting the oxo group into substituent Z.

Referring to Scheme 1, the quinazolinone of formula II is first activated by reacting it with an activating agent at a temperature from about 60° C. to about 120° C., preferably at the reflux temperature, and then adding a reagent of the formula ZH. Examples of appropriate activating agents are the following: triphenylphosphine polymer/carbon tetrachloride in a methylene chloride solvent; phosphorus oxychloride (POCl$_3$) (neat); POCl$_3$ in the presence of pyridine lutidine or another amide base; phosphorus pentachloride (PCl$_5$); oxalyl chloride (COCl)$_2$, using a DMS catalyst; or thionyl chloride (SOCl$_2$) (neat). The reaction with the Z-containing reagent is generally carried out in a C$_1$–C$_6$ alcohol solvent, preferably isopropanol, in a sealed tube at a temperature from about 68° C. to about 120° C., preferably at about 120° C. Prior to adding the Z-containing reagent, the solvent from the activation step is generally removed using a rotary evaporator or, where the activating agent is triphenylphosphine polymer/carbon tetrachloride, by filtration.

Compounds of the formula II can be prepared as illustrated in Scheme 2. Referring to Scheme 2, compounds of the formula III are reacted with a compound of the formula IV in the presence of a palladium (2) catalyst and an inorganic base. This reaction, which forms a bond between the aryl or heteroaryl group and position "6" or "7" of the quinazolinone nucleus, is typically carried out in a solvent such as toluene, benzene or a $C_1$–$C_4$ alcohol, at a temperature from about room temperature to about the reflux temperature of the reaction mixture. It is preferably carried out at the reflux temperature. Examples of catalysts that can be used are palladium diphenylphosphine butane dichloride, bis-(triphenylphosphine)palladium, palladium acetate, and palladium tetrakis triphenylphosphine. Examples of inorganic bases that can be used are sodium hydride, sodium or potassium carbonate, and sodium or potassium hydroxide. The foregoing procedure can also be used to add a second Ar group to the quinazolinone nucleus (i.e., to prepare a compound of formula II in which a substituent Ar is attached both to positions "6" and "8").

Compounds of the formula III can be obtained, as illustrated in Scheme 3, by reacting a compound of the formula V with iodochloride (ICl) in concentrated aqueous hydrochloride acid and ethanol, at a temperature from about –40° to about 20° C., to form the corresponding compounds of formula VI. The resulting compounds of formula VI can then be converted into the desired starting materials of formula III by reacting them in a formamide solvent with HC(=O)NH$_2$ at a temperature from about 120° C. to about 180° C.

Schemes 4 and 5 illustrate methods of preparing, respectively, compounds of formulas IV and II in which Ar is pyridyl. Analogous procedures can be used to prepare the corresponding compounds at the formulas II and IV wherein Ar represents other heteroaryl groups. Referring to Scheme 4, a compound of the formula VI, in which q is zero, one, two or three, is reacted with hexabutyl ditin ($(CH_4H_9)$) $_3SnSn(C_4C_()_3)$ in the presence of palladium tetrakis triphenylphosphine in a polar, aprotic solvent such as tetrahydrofuran (THF), dioxane, diemthylformamide (DMF) or ether, preferably THF or toluene at a temperature from about 20° C. to about the reflux temperature of the reaction mixture, preferably at about the reflux temperature. The compound of formula VII so formed can then be converted into the corresponding compound of formula IVA by reacting it first with n-butyl lithium and trimethyox borate (B(OCH)$_3$) or triisopropoxy borate (B(OCH(CH$_3$)$_2$)$_3$), and then with hydrochloric acid. Generally, this reaction, which can also be used to convert compounds of the formula VI directly into the corresponding compounds of formula IVA, as shown in Scheme 4, is generally carried in a polar, aprotic solvent such as THF, dioxane, ether, DMF or glyme, preferably THF or ether, at a temperature from about –100° C. to about –40° C., preferably at about –78° C.

Referring to Scheme 5, a compound of formula VII, wherein q is zero, one, two or three, is reacted with a compound of the formula III to form the desired compound of formula IIA wherein a substituted or unsubstituted pyridyl group is directly attached to the quinazolinone nucleus. Typically, this reaction is carried out in the presence of a palladium (0) catalyst such as palladium tetrakis triphenylphosphine in a polar aprotic solvent such as THF, dioxane, ether, glyme or DMF, preferably THF, a temperature from about 20° C. to about the reflux temperature of a reaction mixture, preferably at about the reflux temperature. The foregoing procedure can also be used to add a second Ar group to position "6" or "7" of the benzo ring.

Scheme 6 illustrates the preferred method for attaching phenyl or naphthyl groups to the benzo moiety of the quinazolinone nucleus. According to this method, this zinc substituted Ar group of formula IX, rather than the tributyl tin substituted Ar group of formula VII, is coupled with the iodine substituent of the compound of formula III. The zinc derivative of formula IX is formed by reacting the corresponding compound of formula VIII with tributylithium and zinc dichloride at a temperature from about –100° C. to about –40° C., preferably at about –78° C. The preferred solvents for this reaction are THF and ether; however, other polar, aprotic solvent such as DMF or dioxane may also be used. The foregoing procedure can also be used to add a second Ar group to position "6" or "7" of the benzo ring.

Compounds of the formula I wherein X is $C_2$ alkene or $C_2$ alkyne can be prepared as illustrated in Scheme 7. These compounds, referred to in Scheme 7 and throughout this specification as compounds of the formula IB, contain an alkenyl, alkynyl or anlynyl-Y linking group between each Ar substituent and the benzo moiety of the quinazoline ring. According to this procedure, the Z substituent is added prior to adding the Ar substituent or substituents. The first reaction illustrated in the Scheme, i.e., the conversion of compounds of the formula III into compounds of the formula VIII, is accomplished using the same procedure illustrated in Scheme 1 and described above for formation of compounds of the formula IA from compounds of the formula II. After the Z substituent has been added at position "4" of the quinazoline ring, the compound of formula VIII is reacted with a compound of the formula Ar—Y—XH, wherein X is $C_2$ alkene or $C_2$ alkyne, to form the desired compound of formula IB. Examples of these two variations of this procedure are illustrated in Schemes 8 and 9, respectively.

The starting materials of formula Ar—Y—XH wherein X is —CH=CH— or —C≡C— are either commercially available or can be prepared using literature methods well known of those of skill in the art or can be prepared by refluxing a compound of the formula ArBr with a compound of the formula XSnBu$_3$ (wherein Bu is butyl) in a toluene or benzene solvent in the presence of palladium diphenylphosphine butane dichloride.

The starting materials of formula ZH are either commercially available or can be prepared using literature methods well known to those of skill in the art or using methods described in PCT Patent Application PCT/IB95/07881, which designates the United States and was filed on Jun. 7, 1995. The foregoing patent application is incorporated herein by reference in its entirety.

Starting materials, the synthesis which is not specifically [described, above, are either commercially available or can be prepared using literature methods well known to those of skill in the art.

The preparation of compounds of the formula I not specifically described in the foregoing experimental section can be accomplished using combinations of the reactions described above that will be apparent to those skilled in the art.

In each of the reactions discussed or illustrated in Schemes 1–9 above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solution of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The active compounds of this invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. In particular, the compounds of this invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The active compounds may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, compounds of formula I may have therapeutic utility in inflammatory, angiogenic and immunologic disorders involving both identified and as yet unidentified tyrosine kinases that are inhibited by compounds of the formula I.

The in vitro activity of the active compounds in inhibiting the receptor tyrosine kinase (and thus subsequent proliferative response, e.g., cancer) may be determined by the following procedure.

Activity of the active compounds, in vitro, can be determined by the amount of inhibition of the phosphorylation of an exogenous substrate (e.g., $Lys_3$—Gastrin or polyGluTyr (4:1) random copolymer (I. Posner et al., *J. Biol. Chem.* 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology* 146, 82–88 (1987) from A431 cells (American Type Culture Collection, Rockville, Md.) and preincubated in a microfuge tube with EGF (2 μg/ml) in phosphorylation buffer + vanadate (PBV: 50 mM HEPES, pH 7.4; 125 mM NaCl; 24 mM $MgCl_2$; 100 μM sodium orthovanadate), in a total volume of 10 μl, for 20–30 minutes at room temperature. The test compound, dissolved in dimethylsulfoxide (DMSO), is diluted in PBV, and 10 μl is mixed with the EGF receptor/EGF mix, and incubated for 10–30 minutes at 30° C. The phosphorylation reaction is initiated by addition of 20 μl $^{33}$P-ATP/substrate mix (120 μM $Lys_3$-Gastrin (sequence in single letter code for amino acids, KKKGPWLEEEEEAYGWLDF), 50 mM Hepes pH 7.4, 40 μM ATP, 2 μCi y-[$^{33}$P]-ATP] to the EGFr/EGF mix and incubated for 20 minutes at room temperature. The reaction is stopped by addition of 10 μl stop solution (0.5M EDTA, pH 8; 2 mM ATP) and 6 μl 2N HCl. The tubes are centrifuged at 14,000 RPM, 4° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$-P] incorporated is measured by liquid scintillation counting. Incorporation in the absence of substrate (e.g., $lys_3$-gastrin) is subtracted from all values as a background and percent inhibition is calculated relative to controls without test compound present.

Such assays, carried out with a range of doses of test compounds, allow the determination of an approximate $IC_{50}$ value for the in vitro inhibition of EGFR kinase activity. The compounds of the formula I that were tested using the procedure described above exhibited $IC_{50}$ values in the range of 0.0001–30 μM.

Activity of the active compounds, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)**, 5, 169–186 (1975), with slight modification. Tumors are induced in the left flank by s.c. injection of $1 \times 10^6$ log phase cultured tumor cells (human MDA-MD-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic® P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length×

[width]$^2$)/2, according to the methods of Geran, R. I., et al. "Protocols for Screening Chemical Agents and Natural Products Against Animal Tumors and Other Biological Systems", Third Edition, *Cancer Chemother. Rep.,* 3, 1–104 (1972). Results are expressed as percent inhibition, according to the formula: Inhibition (%)=(TuW$_{control}$–TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates. The title compounds of the experimental examples of this case that are compounds of the formula I all exhibited, when tested in the above assay, percent inhibition values greater than 50% at 10 $\mu$M.

Administration of the active compounds can be effected by any method that enables delivery of the compounds to the site of action (e.g., cancer cells). These methods include oral routes, intraduodenal routes, parenteral injection (including intravenous, subcutaneous, intramuscular, intravascular or infusion), topical administration, etc.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences,* Mack Publishing Compnay, Easter, Pa., 15th Edition (1975).

EXAMPLE 1

(1H-Indol-5-yl)-(6-iodo-quinazolin-4-yl)-amine

6-Iodo-3H-quinazolin-4-one (50 gm, 18.3 mmol) was slurried in 60 mL methylene chloride ($CH_2Cl_2$) with several drops of DMF. Oxalyl chloride (6.99 g, 4.83 mL, 55.1 mmol) was added dropwise to the slurry at 0° C. The reaction was refluxed for 48 hours and then concentrated in vacuo. Pyridine (2.9 gm, 2.97 mL, 36.7 mmol) and tert-butyl alcohol (10 mL) was added to dissolve the 4-chloro-6-iodo quinazoline. 5-Aminoindole (2.9 gm, 22.0 mmol) was added and the reaction was heated to 60° C. overnight. Diluted the reaction mixture with chloroform ($CHCl_3$) and washed with brine, saturated aqueous $NaCHO_3$ and dried over $NaSO_4$. The organic layer was concentrated in vacuo to a black oil. The crude product was chromatographed on silica gel (2 parts methanol to 1 part methylene chloride (2 MeOH/$CH_2Cl_2$)) to provide 2.99 gm of white crystalline product.

M.P. 261° C.; LC-MS; 387 ($M^+$); RP18-HPLC RT: 4.12 min.

EXAMPLE 2

(1H-Indol-5-yl)-(6-phenylethynyl-quinazolin-4-yl)-amine (1H-Indol-5-yl)-(6-iodo-quinazolin-4-yl)-amine (200 mg, 0.5 mmol), 1-ethynylbenzene (158 mg, 1.5 mmol) and diethyl amine (189 mg, 2.5 mmol) were combined in 4 mL of DMF. Copper iodide (16 mg, 0.09 mmol) and bis-triphenyl phosphine dichloropalladium (18 mg, 0.025 mmol) were added to the reaction. The reaction was sealed under nitrogen and wrapped in aluminum foil and heated to 60° C. for 2 hours. The reaction was cooled to room temperature and diluted with chloroform. The mixture was washed with 1N EDTA solution, saturated aqueous sodium bicarbonate ($NaHCO_3$) and dried over sodium sufate ($Na_2SO_4$). The organic layer was concentrated in vacuo to afford a brown oil. The crude product was chromatographed on silica gel using 2% methanol/chloroform to provide 186 mg (quantitative yield) of pure produce as its free base.

The yellow residue was slurried in $CHCl_3$/MeOH and 2 equivalents of 1N HCl/ether was added. The title compound was precipitated with ether to produce 155 mg, 69%).

M.P. 278–287° C. (dec); LC-MS: 361 ($M^+$); RP18-HPLC RT: 5.05 min.

EXAMPLE 3

6-Iodo-7-methoxy-3H-quinazolin-4-one

2-Ethylcarboxy-5-methoxyaniline (anthranilie) (10 gm, 43 mmol) is dissolved in 50 mL of water, 30 mL of ethanol and 4.3 mL concentrated hydrochloric acid (HCl). The solution is cooled to 20° C. A solution of iodomonochloride (7.0 gm, 43.1 mmol in 7.55 mL concentrated HCl and 27 mL water) at 5° C. is added quickly to the aniline solution. The reaction is stirred overnight. Filtered the reaction to obtain 20.5 gm (96%) of product which was used as is in the next step.

Dimethylformamide dimethoxyacetal (59.1 gm, 496 mmol) is added to the product and the solution is heated for 14 hours at 80° C. Concentrated the reaction in vacuo and dissolved in methanol (100 mL) and cooled to 0° C. Ammonia was bubbled through the solution for 45 min. The reaction stirred at room temperature overnight. 6-iodo-7-methoxy quinazoline was filter from the reaction as pure product (20.9 gm, 84%).

EXAMPLE 4

(1H-Indol-5-yl)-(6-iodo-7-methoxy-quinazolin-4-yl)-amine

In a round bottom flask 6-Iodo-7-methoxy-3H-quinazolin-4-one (500 mg, 1.65 mmol), triphenyl phosphine polymer (2.75 gm, 3 mmol/gm) and carbon tetrachloride (2.53 gm, 16.5 mmol) were combined in 3 mL of dichloroethane and heated at reflux for 5 hours. 5-Aminoindole (686 mg, 1.65 mmol) was added to the mixture and heated at 50° C. overnight. Reaction mixture was concentrated in vacuo and the residue was chromatographed on silica gel 20% MeOH/1% ammonium hydroxide ($NH_4OH$)/$CHCl_3$ to provide 186 mg (28%) of product as a pale yellow solid.

M.P. 260–267° C.; PB-MS: 417 ($MH^+$); RP18-HPLC RT: 4.28 min.

EXAMPLE 5

(6-Ethynyl-7-methoxy-quinazolin-4-yl)-(1H-indol-5-yl)-amine

The trimethylsilyl protected title compound was synthesized according to the method of example 2 using (1H-Indol-5-yl)-(6-iodo-7-methoxy-quinazolin-4-yl)-amine (90 mg, 0.198 mmol), trimethylsilyl acetylene (59 mg, 0.596 mmol) and diethylamine (72 mg, 0.99 mmol) in 2 mL of DMF. The trimethylsilyl group was removed by addition of solid tetra-n-butyl ammonium fluoride hydrate (155 mg). The mixture stirred for 1 hour and was diluted with ethyl acetate. The organic layer was dried over $Na_2SO_4$ and concentrated in vacuo to provide a yellow oil. The crude product was chromatographed on silica gel using 5% MeOH/$CH_2Cl_2$ to afford 44 mg of product as free base. The HCl salt was made as in the method of example 1 to give 34 mg (49%) of the title compound.

M.P. 176° C.; LC-MS: 350 ($MH^+$); RP18-HPLC RT: 3.48 min.

EXAMPLE 6

(1H-Indol-5-yl)-[&-methoxy-6-(2-pyridin-4-yl-vinyl)-quinazolin-4-yl]-amine

In a sealed tube under nitrogen, (1H-Indol-5-yl)-(6-iodo-7-methoxy-quinazolin-4-yl)-amine (80 mg, 0.176 mmol), 4-vinylpyridine (22 mg, 0.211 mmol), palladium acetate (4 mg, 0.001 mmol) and triethylamine (74 mg, 103 µL, 0.74 mmol) were combined in 1.5 mL of acetonitrile. The reaction was heated at 100° C. for 48 hours. Filtered crude product from reaction mixture and chromatographed on silica gel 10% MeOH/$CHCl_3$ to obtain 60 mg of product as the free base. The title compound was converted to 56 mg (68%) of its HCl salt as described in Example 2.

M.P. 264–273° C. (dec); TS-MS:394 ($M^+$); RP18-HPLC RT: 3.98 min.

The compounds of Examples 7–18 were made according to the method of Example 6 from (1H-Indol-5-yl)-(6-iodo-7-methoxy-quinazolin-4-yl)-amine and appropriate vinyl staring materials.

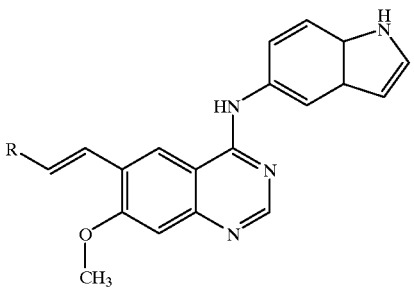

| Example # | R | Yield | HPLC RT | LC/MS $M^+$ |
|---|---|---|---|---|
| 7 | phenyl | 100 | 5.893 | 393.2 |
| 8 | 4-methoxyphenyl | 100 | 5.893 | 423.2 |
| 9 | 3,4-dimethoxyphenyl | 100 | 5.228 | 453.3 |
| 10 | 4-phenyl-methanol | 69 | 4.055 | 423.2 |
|  | 4-benzyloxy-3-methoxy-phenyl | 55 | 7.020 | 529.3 |
| 11 | 4-amino-phenyl | 88 | 3.79 | 408.2 |
| 12 | 2-pyrazin-2-yl | 34 | 6.25 | 394.2 |
| 13 | 7-methoxy-6-(2-pyridin-2-yl | 10 | 5.967 | 394.2 |
| 14 | 5,5,8,8-tetramethyl-5,6,7,8-tetrahydro-naphthalen-2-yl | 46 | 5.952 | 503.4 |
| 15 | 2-nitro-phenyl-acetamide | 15 | 4.923 | 495.3 |
| 16 | 2-6-methyl-1-oxy-pyridin-3-yl | 50 | 2.907 | 424.3 |
| 17 | 4-(1-Amino-ethyl)-phenyl | 35 | 3.235 | 436.2 |
| 18 | 3,5-Dimethoxy-phenyl | 89 | 5.910 | 453.3 |

EXAMPLE 19

(1H-Indol-5-yl)-[6-(2-pyridin-2-yl-vinyl)-quinazolin-4-yl]-amine

The title compound was prepared according to the method in Example 6 using (1H-Indol-5-yl)-(6-iodo-quinazolin-4-yl)-amine (200 mg, 0.52 mmol) and 2-vinylpyridine (65 mg, 67 uL, 0.62 mmol).

M.P. 300° C. (dec); PM-MS:364 ($MH^+$); RP18-HPLC RT: 3.83 min.

EXAMPLE 20

6-(2-Pyridin-4-yl-vinyl)-3H-quinazolin-4-one

In a sealed tube under nitrogen, 6-iodoquinazolone (1.36 gm, 5.0 mmol), 4-vinylpyridine (631 mg, 6.0 mmol), palladium acetate (11 mg, 0.05 mmol) and triethyl amine (1.11 gm, 1.53 mL, 11 mmol) were combined in 7 mL of acetonitrile and heated at 100° C. for 18 hours. The reaction mixture was cooled to room temperature and the product was isolated by filtration. The product was washed with acetonitrile and dried in vacuum oven to provide 536 mg (43%) of a white solid.

M.P. 307–309° C., TS-MS:250 ($MH^+$); RP18-HPLC RT: 2.41 min.

EXAMPLE 21

(3-Ethynyl-phenyl)-[6-(2-pyridin-4-yl-vinyl)-quinazolin-4-yl]-amine

The title compound (250 mg, 1.0 mmol) from Example 20, triphenyl phosphine polymer (1.66 gm, 3 mmol/g resin), and carbon tetrachloride (1.53 gm, 10.0 mmol) were combined in 3 mL of dichloroethane and heated at 60° C. overnight. 3-ethynyl aniline (152 mg, 1.3 mmol) was added and the reaction continued at 60° C. for 3 hours. The reaction mixture was cooled to room temperature and the resin was filtered off and the solution was concentrated in vacuo. A yellow solid was obtained which was washed with methanol MeOH and hot methylene chloride $CH_2Cl_2$, and dried to obtain 290 mg (68%) of product as its free base. 140 mg of the free base was converted to the title compound (166 mg, 39%) following the method of Example 2.

M.P. 272° C. (dec); PB-MS:349 (MH$^+$); RP18-HPLC RT: 4.86 min.

EXAMPLE 22

(1H-Indol-5-yl)-[6-(2-pyridin-4-yl-vinyl)-quinazolin-4-yl]-amine

The title compound (250 mg, 1.0 mmol) from Example 20 was activated in an analogous method to Example 21 and combined with 5-aminoindole (171 mg, 1.3 mmol). The reaction mixture was heated at 60° C. overnight and then cooled to room temperature. The resin was filtered off and the solution was concentrated in vacuo. The crude residue was chromatographed on silica gel in 10% acetone/ethyl acetate to provide 270 mg (74%) of the product.

M.P. 290° C. (dec); TS-MS: 364 (MH$^+$); RP18-HPLC RT=3.71 min.

EXAMPLE 23

(3-Oxazol-5-yl-phenyl)-[6-(2-pyridin-4-yl-vinyl)-quinazolin-4-yl]-amine

The title compound (200 mg, 0.8 mmol) from Example 20 was activated in an analogous method to Example 21 and combined with 3-oxazolo-aniline (128 mg, 0.8 mmol) and heated at 60° C. for 48 hours. The reaction was cooled to room temperature, the resin was filtered off and the solution was washed with saturated aqueous $NaHCO_3$ dried over $Na_2SO_4$ and concentrated in vacuo. The crude residue was chromatographed on silica gel with 5% $MeOH/CH_2Cl_2$ and then chromatographed on RP18 HPLC with ammonia acetate (pH 4.5)/acetonitrile to produce a yellow residue. The residue was converted to the title compound (34 mg, 7%) following the method of Example 2.

M.P. 285° C. (dec); PB-MS:392 (M$^+$); RP18-HPLC R.T.= 4.07 min.

EXAMPLE 24

(1H-Indol-5-yl)-[6=(2-pyridin-2-yl-vinyl)-quinazolin-4-yl]-amine

In a sealed tube under nitrogen, (1H-Indol-5-yl)-(6-iodo-quinazolin-4-yl)-amine (80 mg, 0.176 mmol), 4-vinylpyridine (22 mg, 0.211 mmol), palladium acetate (4 mg, 0.001 mmol) and triethylamine (74 mg, 103 µL, 0.74 mmol) were combined in 1.5 mL of acetonitrile. The reaction was heated at 100° C. for 48 hours. Filtered crude product from reaction mixture and chromatographed on silica gel 10% $MeOH/CHCl_3$ to obtain 60 mg of product as the free base. The title compound was converted to 56 mg (68%) of its HCl salt as described in Example 2.

M.P. 264–273° C. (dec); TS-MS:394 (M$^+$); RP18-HPLC RT: 3.98 min.

EXAMPLE 25

7-Methoxy-6-pyridin-2-yl-3H-quinazolin-4-one

To a flame dried 3 neck round bottom flask, 2-bromopyridine (3.14 gm, 19.9 mmol) was added to 40 ml of tetrahydrofuran and the solution was cooled to −78° C. n-Butyllithium (12.4 mL, 19.9 mmol, 1.6 M) was added dropwise and the reaction stirred for 20 minutes. Zinc chloride (39.7 mL, 0.5 M, 19.9 mmol) was added at −78° C., the mixture continued to stir for 5 min and then was warmed to room temperature to produce a light green solution of zinc pyridyl intermediate.

Palladium diphenylphosphinyl butane bischloride was prepared in situ by mixing equimolar amounts of palladium diphenylphosphine bischloride (282 mg, 0.66 mmol) and diphenylphosphinyl butane (254 mg, 0.66 mmol) in 40 mL, of the THF for 20 min. 6-iodo-7-methoxyquinazoline (2.0 gm, 6.6 mmol) was added followed by the zinc pyridyl solution and the reaction mixture was refluxed for 24 hours. The reaction was concentrated in vacuo and chromatographed on silica gel with 10% ethanol/$CHCl_3$ to provide 1.83 g (quantitative) the title compound.

M.P.: 302° C. (dec.); TS-MS:254 (MH$^+$); RP18-HPLC RT=2.42 min.

EXAMPLE 26

(1H-indol-5-yl)-(7-methoxy-6-pyridin-2-yl-quinazolin-4-yl)-amine

The title compound of Example 25 (300 mg, 1.2 mmol), trihenylphosphine polymer (1.97 gm, 3 mmol/gm resin), and carbon tetrachloride (1.8 gm, 1.14 ml, 11.8 mmol) were combined in 10 ml dichloroethane and heated to 85° C. for 48 hours. The resin was filtered off and the solution added to 5-aminoindole (156 mg, 1.18 mmol). The solution refluxed for 16 hours and cooled to room temperature and concentrated in vacuo to a yellow residue. The crude product was chromatographed on silica gel using ethyl acetate and provided 25 mg (5%) of the title compound.

M.P. 194 (dec); APC-MS:368 (MH$^+$); RP18-HPLC RT=3.66 min.

EXAMPLE 27

(3-Bromo-phenyl)-(7-methoxy-6-pyridin-2-yl-quinazolin-4-yl)-amine

The title compound of Example 25 (300 mg, 1.2 mmol), triphenylphosphine polymer (1.97 gm, 3 mmol/gm resin), and carbon tetrachloride (1.8 gm, 1.14 ml, 11.8 mmol) were combined in 10 ml dichloroethane and heated to 85° C. for 48 hours. The resin was filtered off and the solution added to 3-bromoaniline (156 mg, 1.18 mmol). The solution refluxed for 16 hours and cooled to room temperature and concentrated in vacuo to a yellow residue. The crude product was chromatographed on silica gel using ethyl acetate and provides 25 mg (5%) of the title compound.

M.P. 231° C. (dec); PB-MS; 407 (MH$^+$); RP18-HPLC RT=4.55 min.

EXAMPLE 28

(1H-indol-5-yl)-[6-(2-pyridin-2-yl-vinyl)-quinazolin-4-yl]-amine

In a selected tube under nitrogen (1H-indol-5-yl)-(6-iodo-quinazolin-4-yl)-amine (200 mg 0.517 mmol), 4-vinylpyridine (65 mg, 0.621 mmol), palladium acetate (12 mg, 0.005 mmol), triphenyl phosphine (27 mg, 0.01 mmol), tetrabutyl ammonium chloride (152 mg, 0.517 mmol) and triethylamine (115 mg, 158 µL, 1.31 mmol were combined in 1.5 mL of acetonitrile. The reaction was heated at 100° C.

for 48 hours. The crude product from the reaction mixture was filtered and chromatographed on silica gel (10% MeCH/CHCl₃) to obtain 60 mg of product as the free base. The title compound was converted to 117 mg (63%) of its HCl salt as described in Example 2.

M.P. 300° C. (dec); TS-MS:364 (M⁺⁺), RP18-HPLC RT: 3.83 min.

The compounds of Examples 29–31 were made according to the method of Example 28 from (1H-indol-5-yl)-(6-iodo-quinazolin-4-yl)-amine and appropriate vinyl starting materials.

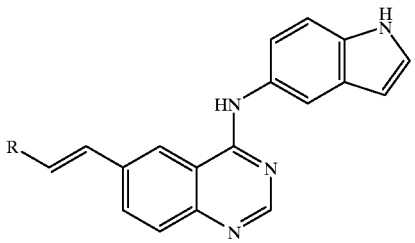

| Example # | R | Yield | HPLC RT | LC/MS M⁺ |
|---|---|---|---|---|
| 29 | 4-phenyl-methanol | 73 | 4.053 | 393.2 |
| 30 | 2-pyrazinyl | 30 | 5.893 | 364.2 |
| 31 | 2-6-methyl-1-oxy-pyridin-3-yl | 70 | 2.923 | 394.2 |

EXAMPLE 32

(1H-Indol-5-yl)-(6-pyridin-2-yl-quinazolin-4-yl)-amine

The title compound of Example 25 (300 mg., 1.2 mmol), triphenylphosphine polymer (1.97 gm, 3 mmol/gm resin), and carbon tetrachloride (1.8 gm, 1.14 ml, 11.8 mmol) were combined in 10 ml dichloroethane and heated to 85° C. for 48 hours. The resin was filtered off and the solution added to 5-aminoindole (156 mg, 1.18 mmol). The solution refluxed for 16 hours and cooled to room temperature and concentrated in vacuo to a yellow residue. The crude product was chromatographed on silica gel using ethyl acetate and provided 25 mg (6%) of the title compound.

M.P. 272–279° C. (dec); APC-MS:338 (MH⁺); RP18-HPLC RT=3.46 min.

EXAMPLE 33

4-[4-(1H-indol-5-ylamino)-quinazolin-6-yl]-benzoic acid ethyl ester

The catalyst Pd(dppb)Cl₂ was prepared according to the method in Example 25 in a lame dried round bottom flask under nitrogen. (1H-indol-6-yl)-(6-iodo-quina-zolin-4-yl)-amine (200 mg, 0.517 mmol) and 4-zinc-iodo-benzoic acid ethyl ester (1.6 ml, 0.6 M, 1.1 mmol) were added and the reaction mixture was refluxed for 24 hours. The reaction was quenched with saturated aqueous ammonium chloride (NH₄Cl) and extracted with ethyl acetate and CH₂Cl₂. The organic extracts were combined and dried over MgSO₄ and concentrated in vacuo in a yellow oil. The crude mixture was chromatographed on silica gel using a gradient of CH₂Cl₂ to 2% MeOH/CH₂Cl₂ to obtain 78 mg (40%) of the free basis. The title compound was made according to the method in Example 2.

M.P. 266–270° C. (dec). TS-MS:409 (MH⁺); RP-18-HPLC RT; 5.21 min.

EXAMPLE 34

2-(4-Oxo-3,4-dihydro-quinazolin-6-yl)-benzoic acid ethyl ester

6-Iodo-3H-quinazolin-4-one (500 mg, 1.83 mmol) was slurried in 1 mL, of DMF and added to 10 ml, of anhydrous THF. Palladium triphenyl phosphine (106 mg, 0.09 mmol), ethyl 4-zinc-iodo-benzoate (5.22 ml, 0.7 M, 3.66 mmol) were added and the mixture was refluxed for 24 hours. The reaction was quenched with MH₄Cl, extracted with CHCl₃, dried over MgSO₄ and concentrated to a yellow oil. The crude residue was chromatographed on silica gel with ethyl acetate to obtain 367 mg (68%) of the title compound.

M.P. 151–158° C.; TS-MS:295 (MH⁺); RP18-HPLC RT; 3.57 min.

EXAMPLE 35

2-[4-(3-Ethynyl-phenylamino)-quinazolin-6-yl]-benzoic acid ethyl ester 2-(4-Oxo-3,4-dihydro-quinazolin-6-yl)-benzoic acid ethyl ester (135 mg, 0.46 mmol) was activated in an analogous procedure to Example 4 and was filtered into a flask containing 3-ethynyl aniline (54 mg, 0.46 mmol). The yellow mixture stirred for 24 hours at room temperature. The reaction was washed with saturated aqueous NaHCO₃, dried over Na₂SO₄ and chromatographed on silica gel using 50% ethyl acetate/hexane. Sixty-four milligrams (35%) of the free base was obtained and the title compound was prepared using a procedure analogous to that of Example 2.

M.P. 174–177° C.; TS-MS;394 (MH⁺); RT18-HPLC RT; 5.66 min.

EXAMPLE 36

2-[4-(1M-indol-5-ylamino)-quinazolin-6-yl]-benzoic acid ethyl ester 2-(4-Oxo-3,4-dihydro-quinazolin-6-yl)-benzoic acid ethyl ester (175 mg, 0.59 mmol) was activated in an analogous procedure to Example 4 and was filtered into a flask containing 5-aminoindole (19 mg, 0.59 mmol). The yellow mixture was stirred for 24 hours at room temperature. The reaction was washed with saturated aqueous NaHCO₃, dried over Na₂SO₄ and chromatographed on silica gel using 50% ethyl acetate/hexane. Fifty milligrams (18%) of the free base was obtained and the title compound was prepared using a procedure analogous to that of Example 2.

M.P.; 212–216° C.; AP⁺-MS;409 (MH⁺); RT18-HPLC RT; 4.69 min.

EXAMPLE 37

6-Pyridin-3-yl-3H-quinazolin-4-one

6-Iodo-3H-quinazolin-4-one (4.0 gm, 14.7 mmol), 3-diethylborate pyridine (1.72 gm, 11.75), potassium hydroxide (2.63 gm, 46.95 mmol), tetrabutyl ammonium iodide (2.16 gm, 5.87 mmol) and tetrakis[triphenyl-phosphine] palladium (680 mg, 0.586 mmol) were combined in 70 mL of anhydrous THF and refluxed for 24 hours. The reaction was neutralized with 1.83 mL of acetic acid and filtered product off as a black precipitate. The precipitate was washed with water and THF and then chromatographed on silica gel using 1% pyridine/5% MeCH/CH$_2$Cl$_2$. 1.29 gm (39%) of a pale yellow solid product was obtained.

M.P. 240–246° C.; TS-MS:224 (MH$^+$), RP18-HPLC RT:2.33 min.

EXAMPLE 38

(3-Oxazol-5-yl-phenyl)-(6-pyridin-3-yl-quinazolin-4-yl)-amine

The title compound was made in an analogous method to Example 4 using 6-Pyridin-3-yl-3H-quinazolin-4-one (200 mg, 0.9 mmol) and 3-oxazolylaniline (143 mg, 0.9 mmol). (81 mg, 27%).

M.P.; 309–320° C. (dec.); TS-MS:366 (MH$^+$).

EXAMPLE 39

(3-Ethynyl-phenyl)-(6-pyridin-3-yl-quinazolin-4-yl)-amine

The title compound was made in an analogous method to Example 4 using 6-Pyridin-3-yl-3H-quinazolin-4-one (200 mg, 0.9 mmol) and 3-ethynyl aniline (104 mg, 0.9 mmol). (81 mg, 27%).

M.P.: 276–282° C.; PB-MS:323 (MH$^+$); RP18-HPLC RT; 4.22 min.

EXAMPLE 40

(1H-Indol-5-yl)-(6-pyridin-3-yl-quinazolin-4-yl)-amine

The title compound was made in an analogous method to Example 4 using 6-Pyridin-3-yl-3H-quinazolin-4-one (200 mg, 0.9 mmol) and 5-amino indole (118 mg; 0.9 mmol). (78 mg, 23%).

M.P.: 259–265° C.; PB-MS:388 (MH$^+$); RP18-HPLC RT; 3.32 min.

EXAMPLE 41

7-Methoxy-6-pyridin-3-yl-3H-quinazolin-4-one

The title compound was made utilizing the method of Example 37 from 6-iodo-7-methoxy-3H-quinazolin-4-one (1.5 gm, 4.96 mmol). Two hundred seventy-eight milligrams (22%) of a pale yellow solid was obtained.

M.P. 233° C., MS: 254 (MH$^+$); RP18-HPLC RT; 2.5 min.

EXAMPLE 42

(3-Ethynyl-phenyl)-(7-methoxy-6-pyridin-3-yl-quinazolin-4-yl)-amine

The title compound was made according to the method of Example 4 using 7-Methoxy-6-pyridin-3-yl-3H-quinazolin-4-one (130 mg, 0.513 mmol)and 3-ethynyl aniline (68 mg, 0.513 mmol). Eight milligrams (10%) of a yellow precipitate was obtained.

M.P. 218–226° C. (dec), TS-MS-353 (MH$^+$); RP18-HPLC RT; 4.61 min.

EXAMPLE 43

(1H-indol-5-yl)-(7-methoxy-6-pyridin-3-yl-quinazolin-4-yl)-amine

The title compound was made according to the method of Example 4 using 7-Methoxy-6-pyridin-3-yl-3H-quinazolin-4-one (130 mg, 0.513 mmol) and 5-aminoindole (68 mg, 0.513 mmol). Twenty-eight milligrams (10%) of the free base was obtained; the HCl salt was made according to a procedure analogous to that of Example 2.

M.P. 222° C. (dec), TS-MS:368 (MH$^+$); RP18-HPLC RT; 3.58 min.

EXAMPLE 44

6-Phenyl-3H-quinazolin-4-one

The catalyst was prepared by adding bis-benzonitrile (palladium (II) chloride (140 mg, 0.37 mmol) to a solution of bis-(diphenylphosphine butane) (157 mg, 0.37 mmol) in 18 mL of toluene. The mixture stirred at room temperature for 20 min. 6-iodo-3H-quinazolin-4-one (1.0 gm, 3.67 mmol), phenyl boronic acid (896 mg, 7.35 mmol), 1M aqueous Na$_2$CO$_3$ (3.67 mL, 7.35 mmol) and 9 mL of ethanol were added to the catalyst solution. The reaction mixture was refluxed for 24 hours. Reaction mixture was cooled to room temperature, filtered through celite, washed with saturated aqueous NaHCO$_3$ and dried over Na$_3$SO$_4$. The organic layer was concentrated to a yellow solid and chromatographed on silica gel using 20% hexane/ethyl acetate. Five hundred ten milligrams (63%) of the title compound were isolated.

PB-MS:223 (MH$^+$); RP18-HPLC RT: 3.47 min.

EXAMPLE 45

4-(6-Chloro-2,3-dihydro-indol-1-yl)-6-phenyl-quinazoline

The title compound was prepared in a manner analogous in the method of Example 4 using 6-Phenyl-3H-quinazolin-4-one (250 mg, 1.124 mmol) and 6-chloroindoline (172 mg, 1.124 mmol)). Three hundred eighty-nine milligrams (88%) of a yellow solid was isolated from the reaction mixture.

M.P. 249–255° C., T.S.M.S.; 358, 360 (M$^+$, M$^+2^{+l}$); $_{RP}$18-HPLC RT; 6.59 min.

EXAMPLE 46

7-Methoxy-6-phenyl-3H-quinazolin-4-one

The title compound was made from 6-iodo-7-methoxy-3H-quinazolin-4-one (5.0 gm, 16.55 mmol) and phenyl boronic acid (4.04 gm, 33.1 mmol) utilizing the method of Example 44. The crude product (1.42 gm, 34%), was isolated after silica gel chromatography. The pure product was used in subsequent reactions.

M.P. 258–262° C.; TS-MS:253(M$^+$); MP18-HPLC RT; 3.67 min.

EXAMPLE 47

4-(6-Chloro-2,3-dihydro-indol-1-yl)-7-methoxy-6-phenyl-quinazoline

The title compound was prepared from 7-Methoxy-6-phenyl-3H-quinazolin-4-one (250 mg, 0.99 mmol) and 6-chloroindoline (152 mg, 0.99 mmol) utilizing the method of Example 45 (163 mg, 39%). One hundred sixty-three milligrams (39%) of product was obtained after column chromatography and precipitation as the HCl salt.

M.P. 218–219° C.; M.S. (T.S.); 388, 390 (m$^+$, m$^+$+2); RP18-HPLC RT:7.05 min.

EXAMPLE 48

{6-[3-(Benzyl-methyl-amino)-prop-1-ynyl]-quinazolin-4-yl}-(1H-indol-5-yl)-amine

The title compound was synthesized according to the method of Example 2 using (1H-indol-5-yl)-(6-iodoquinazolin-4-yl)-amine (200 mg, 0.517 mmol), N-Methyl-n-proparglylbenzylamine (246 mg, 1.596 mmol) and diethyl amine (189 gm, 2.59 mmol) in 2 mL, of dimethylformamide (DMF).

M.P. 187° C. (dec.); LC-MS; 418 (MH$^+$); RP18-HPLC RT: 4.13 min.

EXAMPLE 49

(3-Ethynyl-phenyl)-(6-pyridin-2-ylethynyl-quinazolin-4-yl)-amine

The title compound was synthesized according to the method of Example 2 using (3-Ethynyl-phenyl)-(6-iodo-quinazolin-4-yl)-amine (125 mg, 0.506 mmol), 2-ethynyl-pyridine (66 mg, 0.505 mmol) and diethyl amine (72 mg, 0.99 mmol) in 2 mL, of DMF.

M.P. 163–169(C.: LC-MS; 347 (MH$^+$); RP18-HPLC RT; 3.80 min.

EXAMPLE 50

(1H-indol-5-yl)-(6-pyridin-2-ylethynyl-quinazolin-4-yl)-amine

The title compound was synthesized according to the method of Example 2 using (1H-indol-6-iodo-quinazolin-4-yl)-amine (125 mg, 0.505 mmol), 2-ethynyl-pyridine (66 mg, 0.506 mmol) and diethylamine (72 mg, 0.99 mmol) in 2 mL of DMF.

M.P. 189° C. (dec.); LC-MS: 362 (MH$^+$): RP18-HPLC RT: 5.13 min.

EXAMPLE 51

(1H-indol-5-yl)-(7-methoxy-6-pyridin-2-ylethynyl-quinazolin-4-yl)-amine

The title compound was synthesized according to the method of Example 2 using (1H-indol-5-yl)-(6-iodo-7-methoxy-quinazolin-4-yl)-amine (135 mg, 0.486 mmol), 2-ethynyl-pyridine (185 mg, 1.45 mmol) and diethylamine (605 mg, 8.27 mmol) in 2 mL., of DMF.

M.P. 237° C. (dec.); LC-MS: 392 (MH$^+$); RP18-HPLC RT: 4.47 min.

EXAMPLE 52

(1H-indol-5-yl)-[7-methoxy-6-(6-methoxy-pyridin-3-yl)-quinazolin-4-yl]-amine

The title compound was made by a method analogous to that of Example 44 using (1H-indol-5-yl)-(6-iodo-7-methoxy-quinazolin-4-yl)-amine (250 mg, 0.6 mmol) and 3-(2-methoxy-pyridyl) boronic acid (183 mg, 1.2 mmol). 172 mg of a pale yellow product was obtained after silica gel chromatography. This was converted to the title compound according to the method of Example 2.

M.P.: 266–280° C. (dec.); AC$^+$-MS:398 (MH$^+$); RP18-HPLC RT; 4.49 min.

EXAMPLE 53

(1H-Indol-5-yl)-(7-thiophen-2-yl-quinazolin-4-yl)-amine.

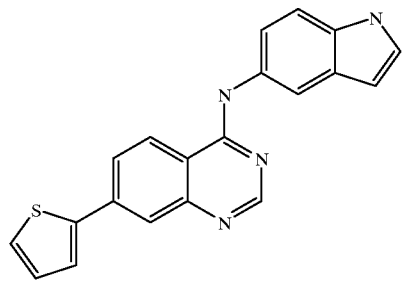

What is claimed is:
1. A compound of the formula:

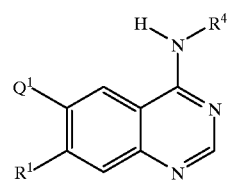

wherein R$^4$ is Q$^2$ substituted by (R$^5$)$_q$;

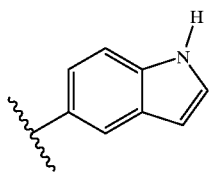

each R$^5$ is independently selected from mono-, di- and tri-fluoromethyl, halo, nitro, hydroxy, amino, azido, isothiocyano, (C$_1$–C$_4$)alkyl, phenyl, thienyl, (C$_1$–C$_4$) alkoxy, benzyloxy, phenoxy, (C$_2$–C$_6$)alkenyl, (C$_2$–C$_6$) alkylnyl, (C$_1$–C$_4$)alkylenedioxy, cyano, benzoylamino, trifluoromethylcarbonylamino, (C$_1$–C$_4$)alkylamino, (C$_1$–C$_4$)alkylsulfonylamino, trifluoromethylsulfonylamino, (C$_1$–C$_4$)alkylthio, (C$_1$–C$_4$)alkylsulfinyl and (C$_1$–C$_4$)alkylsulfonyl, pyrrol-1-yl, piperdin-1-yl and pyrrolidine-1-yl, wherein said phenyl, benzyloxy, phenoxy and benzoylamino may optionally be mono-substituted with halo, nitro, trifluoromethyl, hydroxy or (C$_1$–C$_4$)alkyl, and wherein said (C$_1$–C$_4$)alkylenedioxy is linked at both ends to adjacent carbons on the benzene moiety;

or two R$^5$'s, together with the carbon atoms to which they are attached, form a group selected from imidazole, pyrrolo and pyrazolyl;

q is an integer from 0 to 3;

Q$^1$ is Ar-Y-X;

Ar is pyridyl, thiophenyl or pyrazinyl, wherein Ar may optionally be subsituted with from one to three substituents R$^2$;

X is C$_2$ alkene, C$_2$ alkyne or absent;

Y is (CH$_2$)$_p$ wherein p is 0 to 5 and wherein one or two of the CH$_2$ groups may optionally and independently be replaced by either oxygen, sulfur, SO$_2$, C=O, NH or NCH$_3$;

each $R^1$ is selected from (a) trifluoromethyl, halo, nitro, hydroxy, amino, cyano, $(C_1-C_4)$ alkyl, $(C_1-C_4)$alkoxy, $(C_1-C_4)$ alkoxycarbonyl, thio, $(C_1-C_4)$alkanoyloxy, $C_1-C_4)$ alkanoylamino, carboxy, phenoxy, benzoyloxy, carbamoyl, mono-N and Di-N-N-di$(C_1-C_4)$ alkylcarbamoyl, mono-N and di-N,N-$(C_1-C_4)$ alkylamino, mono-N- and di-N,N-(hydroxy$(C_2-C_4)$ alkyl)amino, mono-N and di-N,N-$(C_1-C_4)$alkoxy $(C_2-C_4)$alkyl)amino, anilino, pyrrolidin-1-yl, piperidin-1-yl, morpholino, piperazin-1yl, 4-$(C_1-C_4)$ alkylpiperazin-1-yl, $C_1-C_4$)alkylthio and phenylthio; and any of the foregoing $R^1$ groups substituted on $(C_1-C_4)$alkyl; and (b) hydroxy$(C_2-C_4)$alkoxy$(C_1-C_4)$alkyl, $(C_1-C_4)$alkoxy-$(C_2-C_4)$alkoxy-$(C_1-C_4)$alkyl, hydroxy$(C_2-C_4)$ alkylthio$(C_1-C_4)$alkyl, $(C_1-C_4)$alkoxy$(C_2-C_4)$ alkylthio$(C_1-C_4)$alkyl, hydroxyamino, benzoylamino, mono-N- and di-N,N-$(C_1-C_4)$ alkylcarbamoylmethylamino, carbamoylmethylamino, $(C_1-C_4)$alkoxcarbonylamino, $(C_1-C_4)$alkanoylamino, carboxymethylamino, $(C_1-C_4)$ alkoxycarbonylmethylamino, $(C_1-C_4)$alkoxyamino, $(C_2-C_4)$alkanoyloxyamino, phenyl$(C_1-C_4)$alkylamino, $(C_1-C_4)$alkylsulphonylamino, benzenesulphonamido, 3-phenylureido, 2-oxopyrrolidin-1-yl, 2,5-dioxopyrroidi-1-yl, uredio, $(C_1-C_4)$alkoxy$(C_1-C_4)$ alkylcarbonylamino, $(C_1-C_4)$alkylsulfinyl, $C_1-C_4$) alkylsulfonyl, $(C_1-C_4)$alkoxy$(C_2-C_4)$alkylthio, mono-, di and trifluoromethyloxy, $(C_1-C_4)$alkylenedioxy, benzyloxy, azido, guanidino, aminocarbonyl, mono-N- and di-N,N-$(C_1-C_4)$alkylaminocarbonyl, phenyl $(C_1-C_4)$alkoxy, carboxymethoxy, $(C_1-C_4)$ alkoxycarbonylmethoxy, carbamoylmethoxy, mono-N and di-N,N-$(C_1-C_4)$ carbamoylmethoxy, mono-N- and di-N,N-$(C_1-C_4)$alkyl carbamoylmethoxy, mono-N- and di-N,N-(hydroxy$(C_2-C_4)$alkyl)carboxamido, mono-N- and di-N,N-(($(C_1-C_4)$alkoxy $(C_2-C_4)$alkyl) carboxamido and bis(($(C_1-C_4)$alkanesulfonyl)amido; and (c) $(C_2-C_4)$alkoxy, $(C_2-C_4)$alkylthio, $(C_2-C_4)$ alkanoyloxy, $(C_2-C_4)$alkylamino, $(C_1-C_4)$alkyl $(C_1-C_4)$alkylenedioxy, and $(C_2-C_4)$alkanoylamino; wherein each of the foregoing $R^1$ groups in "c" may optionally be substituted with one or two substituents independently selected from amino, halo, hydroxy, $(C_2-C_4)$alkanoyloxy, $(C_1-C_4)$alkoxy, mono-N and di-N,N-$(C_1-C_4)$alkylamino, mono-N and di-N,N-(hydroxy$(C_2-C_4)$alkyl)amino, mono-N and di-N,N-(($(C_1-C_4)$alkoxy$(C_2-C_4)$alkyl)amino, $(C_1-C_4)$ alkanoylamino, phenoxy, anilino, imidazol-1-yl, phenylthio, piperidino, morpholine, piperazin-1-yl, 4-$(C_1-C_4)$alkylpiperazin-1yl-, carboxy, $(C_1-C_4)$ alkoxycarbonyl, carbamoyl, mono-N and di-N,N-$(C_1-C_4)$alkylcarbamoyl, carboxamido, mono-N- and di-N,N-$(C_1-C_4)$alkylcarboxamido or mono-N- and di N,N-(hydroxy$(C_2-C_4)$alkyl)carboxamido; wherein any phenyl moiety in an $R^1$ substituent may optionally be substituted with one or two substituents independently selected from halo, nitro, trifluoromethyl, hydroxy, $(C_1-C_4)$alkoxy and $(C_1-C_4)$alkyl, and wherein said $(C_1-C_4)$ alkylenedioxy is linked at both ends to the quinazoline ring; and each $R^2$ is independently selected from the substituents listed above in paragraphs "(a)" and "(b)" of the definition of $R^1$;

and the pharmaceutically acceptable salts of such compounds.

2. A compound according to claim 1 wherein Ar is optionally substituted pyridine or pyrazine.

3. A compound according to claim 1 selected from the group consisting of:

(1H-indol-5-yl)-[7-methoxy-6-(2-pyridin-4-yl-vinyl)-quinazolin-4-yl]-amine;

(1H-indol-5-yl)-(7-methoxy-6-pyridin-3-yl-quinazolin-4-yl)-amine;

(1H-indol-5-yl)-(7-methoxy-6-pyridin-2-yl-quinazolin-4-yl)-amine;

4-(1H-indol-5-ylamino)-6-pyridin-3-yl-quinazolin-7-ol;

(1H-indol-5-yl)-(7-methoxy-6-pyridin-2-yl-ethynyl-quinazolin-4-yl)-amine;

(1H-indol-5-yl)-[7-(2-methoxy-ethoxy)-6-pyridin-3-quinazolin-4-yl]-amine;

(1H-indol-5-yl)-[7-methoxy-6-(2-pyrazin-2-yl-vinyl)-quinazolin-4-yl]-amine;

(1H-indol-5-yl)-{7-methoxy-6-[2-(6-methyl-1-oxy-pyridin-3-yl-vinyl]-quinazolin-4-yl}-amine;

(1H-indol-5-yl)-[7-methoxy-6-(6-methoxy-pyridin-3-yl)-quinazolin-4-yl]-amine; and (1H-indol-5-yl)-[7-methoxy-6-[1-oxy-pyridin-3-yl)-quinazolin-4-yl]-amine.

4. A pharmaceutical composition for the treatment of hyperproliferative diseases in a mammal which comprises a therapeutically effectively amount of a compound of claim 1 and a pharmaceutically acceptable carrier.

5. A compound of the formula

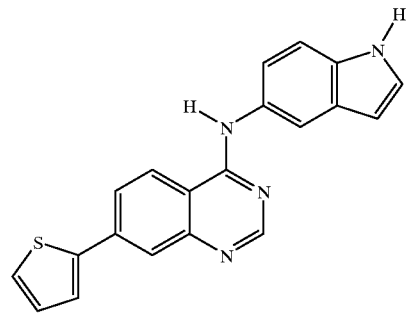

6. A pharmaceutical composition for the treatment of hyperproliferative diseases in a mammal which comprises a therapeutically effective amount of the compound of claim 5 and a pharmaceutically acceptable carrier.

* * * * *